United States Patent [19]

Hajos et al.

[11] Patent Number: 4,482,730

[45] Date of Patent: Nov. 13, 1984

[54] SYNTHESIS OF DIOXABICYCLO[3.2.1]OCTANES AND OXEPANES

[75] Inventors: Zoltan G. Hajos, Princeton; Michael P. Wachter, Bloomsbury, both of N.J.

[73] Assignee: Ortho Pharmaceutical Corporation, Raritan, N.J.

[21] Appl. No.: 475,986

[22] Filed: Mar. 16, 1983

Related U.S. Application Data

[62] Division of Ser. No. 305,019, Sep. 24, 1981, Pat. No. 4,387,234, which is a division of Ser. No. 141,524, Apr. 18, 1980, Pat. No. 4,322,353.

[51] Int. Cl.$^3$ .............................................. C07D 317/00
[52] U.S. Cl. .................................................... 549/448

[58] Field of Search ........................................ 549/448

[56] References Cited

U.S. PATENT DOCUMENTS

| | | | |
|---|---|---|---|
| 2,739,972 | 3/1956 | Abbott et al. | 549/448 |
| 3,873,572 | 3/1975 | Wehrli | 549/448 |
| 4,055,603 | 10/1977 | Johnson et al. | 549/448 |

Primary Examiner—Ethel G. Love
Attorney, Agent, or Firm—Benjamin F. Lambert

[57] ABSTRACT

The synthesis of C-4 alkyl homologs of racemic (1RS,4SR,5RS)-4-(4,8-dimethyl-5-hydroxy-7-nonenyl)-4-methyl-3,8-dioxabicyclo[3.2.1]octane-1-acetic acid and the corresponding (1RS,4RS,5RS) - derivative is described. The dioxabicylo[3.2.1]octanes are useful as contragestational agents.

3 Claims, No Drawings

SYNTHESIS OF DIOXABICYCLO[3.2.1]OCTANES AND OXEPANES

This is a division of application Ser. No. 305,019 filed Sept. 24, 1981 now U.S. Pat. No. 4,387,234 which in turn is a divisional of Ser. No. 141,524 filed 4/18/80 now U.S. Pat. No. 4,322,353.

The synthesis of (1RS,4SR,5RS)-4-(4,8-dimethyl-5-hydroxy-7-nonenyl)-4-methyl-3,8-dioxabicyclo[3.2.1]octane-1-acetic acid (I)

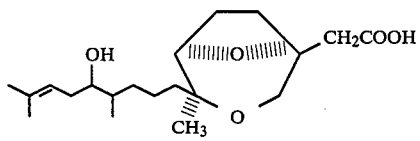
I from the optically active component in the zoapatle plant is described in U.S. Pat. No. 4,102,895. The present invention relates to the C-4 alkyl homologs of racemic (1RS,4SR,5RS)-4-(4,8-dimethyl-5-hydroxy-7-nonenyl)-4-methyl-3,8-dioxabicyclo[3.2.1]octane-1-acetic acid and the corresponding (1RS,4RS,5RS) derivative and to a method of synthesizing the C-4 alkyl homologs. The novel C-4 alkyl homologs which are the subject of this invention have the following chemical configuration.

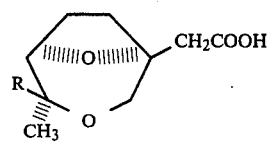
II wherein R is a straight or branched chain alkyl group of from 1–12 carbon atoms such as ethyl, n-propyl, isopropyl, n-butyl, isobutyl, pentyl, hexyl, octyl, nonyl, n-decyl, dimethyl decyl and the like, and the pharmaceutically acceptable acid addition salts thereof. The C-4 alkyl homologs of racemic (1RS,4SR,5RS)-4-(4,8-dimethyl-5-hydroxy-7-nonenyl)-4-methyl-3,8-dioxabicyclo[3.2.1] octane-1-acetic acid are active as contragestational agents.

The novel dioxabicyclo[3.2.1]octanes are prepared by a synthetic route which is comprised of several steps which are summarized in the following schematic diagram:

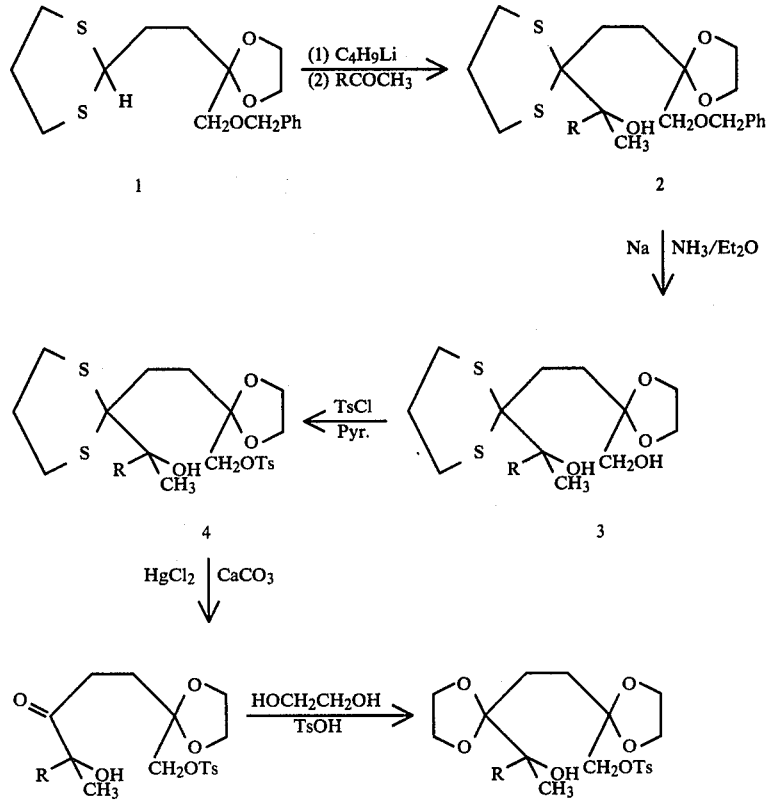

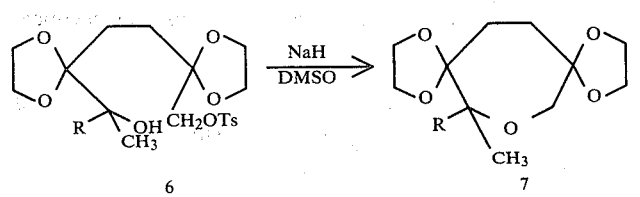
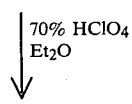
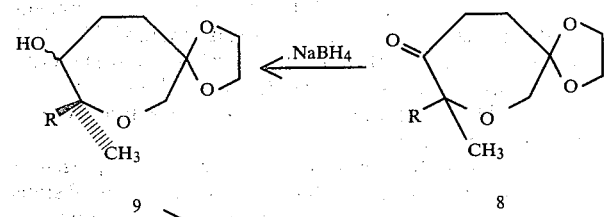
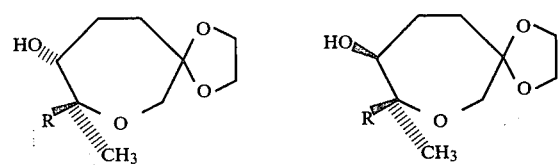
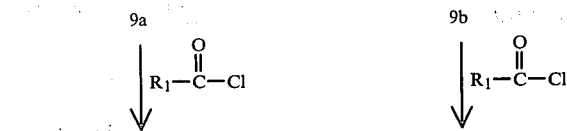
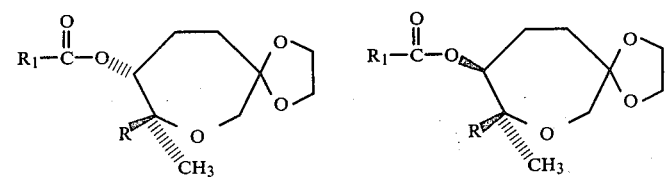
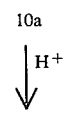 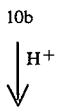
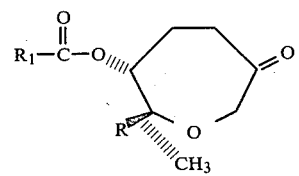 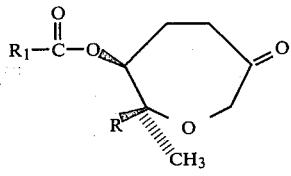

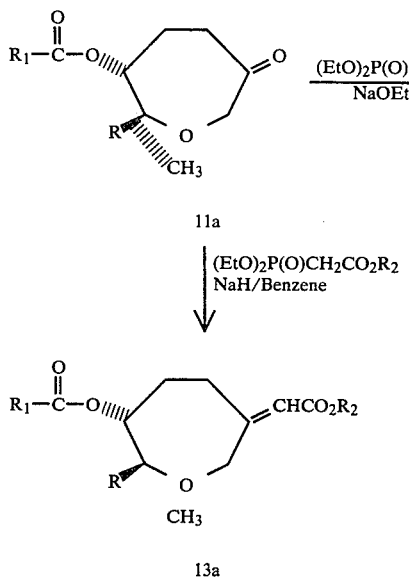

11a (EtO)₂P(O)CH₂CO₂R₂
NaH/Benzene

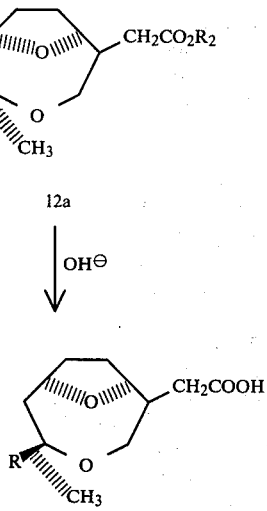

13a wherein R is a straight or branched chain alkyl group of from 1-12 carbon atoms, $R_1$ is a lower alkyl group having 1-6 carbon atoms such as a methyl, ethyl, propyl, butyl, pentyl or hexyl group, $R_2$ is hydrogen or a lower alkyl group having 2-6 carbon atoms, Ph is a phenyl group, Et is ethyl and Ts is a tosyl (p-toluenesulfonyl) group.

The first step in the synthesis of the bicyclic acid (II) involves conversion of the dithiane (1) to the corresponding tertiary alcohol (2). The conversion is achieved by reacting the lithio salt of the dithiane (1) with an alkyl methyl ketone in a suitable solvent such as tetrahydrofuran, dioxane or ether. The reaction is generally carried out at a temperature below 0° C. and preferably at a temperature between −70° C. and 0° C. The lithio salt of the dithiane (1) is prepared by reacting the dithiane (1) with butyllithium in a solvent such as tetrahydrofuran, dioxane or ether. The tertiary alcohol (2) is purified by techniques known to those skilled in the art such as, for example, chromatography. The benzyl group is then removed from the tertiary alcohol (2) by reaction with sodium in liquid ammonia and ether, dioxane or tetrahydrofuran. The primary alcohol of the diol (3) which forms is selectively tosylated by reaction with tosyl chloride in a suitable base such as, for example, pyridine to form the monotosylate (4). The reaction is preferably carried out at room temperature. The dithiane protecting group is then removed by reaction with mercuric chloride and calcium carbonate in aqueous acetonitrile or methyl iodide in acetone to give the corresponding α-hydroxy ketone (5).

The acyclic intermediate (6) is prepared by ketalization of the α-hydroxy ketone (5) by techniques known to those skilled in the art. Cyclization of the acyclic intermediate (6) with sodium hydride in dimethylsulfoxide yields the oxepane (7). The reaction is carried out at a temperature between 20° C. and 100° C. The preferred reaction temperature is about 70° C. Other cyclizing agents which can be employed include potassium hydride, lithium hydride and potassium hydroxide. Selective hydrolysis of the 3-ketal in the oxepane (7) to the keto-ketal (8) is achieved by reaction with an acid such as perchloric acid in a suitable solvent such as ether or boron trifluoride-ethyl ether, for example. The reaction temperature is between room temperature and about 35° C. Reduction of the keto-ketal (8) with a reducing agent such as sodium borohydride, sodium cyanoborohydride, sodium bis(methoxyethoxy) aluminum hydride in a suitable solvent such as methanol, benzene or tetrahydrofuran, for example, gives a mixture of epimeric alcohols (9a and 9b) which can be separated by physical means such as, for example, chromatography. In one of the alcohols (9a) the $C_2$ methyl group and the $C_3$ hydroxyl group are cis, and in the other (9b) these groups are trans. Acylation of the pure alcohols with an acylating group such as acetyl chloride, acetyl bromide or acetic anhydride in a base such as pyridine, for example, yields the corresponding ester (10). Treatment of the ester with an acid such as, for example, hydrochloric acid, in a suitable solvent such as acetone, for example, gives the corresponding acyloxyketone (11). Alternatively, the acyloxyketones (11a and 11b) can be prepared via acylation of the mixture of epimeric alcohols (9) which yields a mixture of esters. Acid hydrolysis of the mixture gives the keto-esters which can be separated by chromatography to give the pure compounds (11a and 11b).

The keto-ester (11a) is then converted to the bicyclic ester (12a) by means of a Wittig reaction employing, for example, triethylphosphonoacetate and sodium ethoxide in a suitable solvent such as ethanol. When the reaction is carried out on the mixture (11a and 11b) the corresponding bicyclic esters are obtained. Alternatively, if the Wittig reaction is carried out with sodium hydride in a suitable solvent such as benzene, toluene or xylene the corresponding α,β-unsaturated ester (13a) or mixture of esters (13a and 13b) is obtained. The ester (12a) is then converted to the free acid (II) by hydrolysis techniques known to those skilled in the art such as hydrolysis with a suitable base such as methanolic sodium hydroxide, for example. The reaction is preferably carried out at a temperature between 0° C. and about 20° C. The free acid (II) and the unsaturated ester (13a) are useful as contragestational agents.

The dithiane which is used as the starting material in the synthesis is prepared by the method described in co-pending application Ser. No. 970,727, filed Dec. 18, 1978, now U.S. Pat. No. 4,239,689.

This invention is further disclosed in the following examples of more preferred embodiments thereof, which are presented for the purpose of illustration and not by way of limiting the scope of the invention.

EXAMPLE 1

1-Benzyloxy-2,2-ethylenedioxy-6-hydroxy-6-methyl-5,5-(1,3-propylenedithio)-nonane (2)

1-Benzyloxy-2,2-ethylenedioxy-4-(1,3-dithian-2-yl)-butane (98.75 g) is treated in distilled tetrahydrofuran (2.5 l) with normal butyllithium (125 ml, 2.5 M in hexane) at −70° C. and allowed to stir below −25° for 2 hours. The solution is cooled to −70° C., methyl propyl ketone (28.75 g) is added and the resulting solution is stirred below 0° C. for 16 hours, concentrated to 250 ml in vacuo and partitioned between ether (500 ml) and brine (500 ml). The aqueous phase is extracted with ether (900 ml) and the combined ether extracts are washed with brine (900 ml), filtered through phase-separating paper and dried (Na$_2$SO$_4$). The solvent is removed in vacuo to give a dark yellow oil (109.6 g) which is purified via chromatography over silica gel (twice) using chloroformhexane as the eluent to give 1-benzyloxy-2,2-ethylenedioxy-6-hydroxy-6-methyl-5,5-(1,3-propylenedithio)-nonane (44 g). A 250 mg portion is further purified on Quantagram LPQ1F plates (ethyl acetate) to give a purified product (225 mg). ir (neat) 2.84μ (OH);

nmr (CDCl$_3$, δ) 0.93 (t, 3H, CH$_3$CH$_2$), 1.32 (s, CH$_3$C$\diagdown^{\diagup}$), 2.8 (m, 4H, SCH$_2$CH$_2$CH$_2$S), 3.31 (s, 2H, OCH$_2$C$\diagdown^{\diagup}$), 3.98

(s, 4H, OCH$_2$CH$_2$O), 4.53 (s, 2H, φCH$_2$O), 7.21 (s, 5H, φCH$_2$O).

When in the above procedure methyl ethyl ketone, methyl butyl ketone, acetone and 2-octanone are employed in place of methyl propyl ketone, 1-benzyloxy-2,2-ethylenedioxy-6-hydroxy-6-methyl-5,5-(1,3-propylenedithio)-octane; 1-benzyloxy-2,2-ethylenedioxy-6-hydroxy-6-methyl5,5-(1,3-propylenedithio)-decane; 1-benzyloxy-2,2-ethylenedioxy-6-hydroxy-6-methyl-5,5-(1,3-propylenedithio) heptane; and 1-benzyloxy-2,2-ethylenedioxy-6-hydroxy-6-methyl-5,5-(1,3-propylenedithio)-dodecane are obtained.

EXAMPLE 2

1,6-Dihydroxy-2,2-ethylenedioxy-6-methyl-5,5-(1,3propylenedithio)-nonane (3)

1-Benzyloxy-2,2-ethylenedioxy-67-hydroxy-6-methyl-5,5-(1,3-propylenedithio)-nonane (34.7 g) is added in ether (500 ml) to distilled liquid ammonia (700 ml). Sodium (5.65 g) is added in portions over a 15 minute period and the reaction mixture is stirred vigorously for 3 hours. Ammonium chloride (15.6 g) is added and the ammonia is allowed to evaporate overnight. Ether and brine are added and after stirring for 45 minutes, the ether layer is removed. The aqueous phase is extracted with ether (1.8 l), and the combined ether extracts are washed with brine, filtered through phase-separating paper and dried (Na$_2$SO$_4$). The solvent is removed in vacuo to give a pale yellow oil (30.3 g). A 300 mg portion of the oil is purified on Quantagram PQ1F plates (ethyl acetate) to give 1,6-dihydroxy-2,2-ethylenedioxy-6-methyl-5,5-(1,3-propylenedithio)-nonane (245 mg). ir (neat 2.88μ (OH);

nmr (CDCl$_3$, δ), 1.1 (t, CH$_3$CH$_2$), 1.35 (s, CH$_3$C$\diagdown^{\diagup}$), 2.82 (m, 4H, SCH$_2$CH$_2$CH$_2$S), 3.5 (s, 2H, HOCH$_2$C$\diagdown^{\diagup}$), 4.0 (s, 4H,

OCH$_2$CH$_2$O).

When in the above procedure 1-benzyloxy-2,2-ethylenedioxy-6-hydroxy-6-methyl-5,5-(1,3-propylenedithio)-octane; 1-benzyloxy-2,2-ethylenedioxy-6-hydroxy-6-methyl-5,5-(1,3-propylenedithio)-decane; 1-benzyloxy-2,2-ethylenedioxy-6-hydroxy-6-methyl-5,5-1,3-propylenedithio)-undecane and 1-benzyloxy-2,2-ethylenedioxy-6-hydroxy-6-methyl-5,5-(1,3-propylenedithio)-dodecane are employed in place of 1-benzyloxy-2,2-ethylenedioxy-6-hydroxy-6-methyl-5,5-(1,3-propylenedithio)nonane, the corresponding octane, decane, undecane and dodecane are obtained.

EXAMPLE 3

2,2-Ethylenedioxy-6-hydroxy-6-methyl-5,5-(1,3-propylenedithio)-1-tosyloxy-nonane (4)

1,6-Dihydroxy-2,2-ethylenedioxy-6-methyl-5,5-(1,3-propylenedithio)-nonane (7.7 g) is treated in dry pyridine (50 ml) with p-toluenesulfonyl chloride (5.8 g) in pyridine (15 ml) and the mixture is allowed to stir overnight at room temperature. The reaction mixture is then partitioned between ether (100 ml) and water (100 ml) and the organic phase is separated, treated with a saturated copper sulfate solution to remove pyridine, washed with brine and filtered through phase-separating paper and dried (Na$_2$SO$_4$). The solvent is removed in vacuo to give a crude oil which is purified via silica gel chromatography using chloroform as the eluent to give crude product (5.43 g). A 200 mg portion is further purified on Quantagram PQ1F plates (5% ethyl acetate/CHCl$_3$) to give 2,2-ethylenedioxy-6-hydroxy-6-methyl-5,5-(1,3-propylenedithio)-1-tosyloxy-nonane (116 mg). ir (neat) 2.83μ (OH), 6.25μ (C=C);

nmr (CDCl$_3$, δ), 1.3 (s, CH$_3$C—), 2.02 (s, $^{\diagdown}$—C—CH$_2$CH$_2$C$\diagdown^{\diagup}$),
$\diagup$ 2.42 (s, 3H, CH$_3$φ), 2.8 (m, 4H, SCH$_2$CH$_2$S), 3.88 (s, 6H, OCH$_2$CH$_2$O and TsOCH$_2$C), 7.45 (q, 4H, CH$_3$φSO$_2$).

When in the above procedure 1,6-dihydroxy-2,2-ethylenedioxy-6-methyl-5,5-(1,3-propylenedithio)-octane; 1,6-dihydroxy-2,2-ethylenedioxy-6-methyl-5,5-(1,3-propylenedithio)-decane and 1,6-dihydroxy-2,2-ethylenedioxy-6-methyl-5,5-(1,3-propylenedithio)- undecane are employed in place of 1,6-dihydroxy-2,2-ethylenedioxy 6-methyl-5,5-(1,3-propylenedithio)- nonane, 2,2 ethylenedioxy-6-hydroxy-6-methyl-5,5-(1,3-propylenedithio)-1-tosyloxy-octane; 2,2-ethylenedioxy- 6-hydroxy-6-methyl-5,5-(1,3-propylenedithio)-1-tosyloxy-decane and 2,2-ethylenedioxy-6-hydroxy-6-methyl-5,5-(1,3-propylenedithio)-1-tosyloxy-undecane are obtained.

EXAMPLE 4

2,2-Ethylenedioxy-6-hydroxy-6-methyl-5-oxo-1-tosyloxynonane (5)

2,2-Ethylenedioxy-6-hydroxy-6-methyl-5,5-(1,3-propylenedithio)-1-tosyloxy-nonane (29.0 g) in 80% aqueous acetonitrile (830 ml) is added dropwise to a mixture of mercuric chloride (33.4 g), calcium carbonate (12.25 g) and 80% aqueous acetonitrile (550 ml) and the resulting slurry is refluxed for 8 hours. The reaction mixture is filtered through a bed of celite and washed with 1:1 chloroform/hexane (3 l). The organic phase is separated, washed with 5M ammonium acetate (700 ml), brine (1 l) and dried ($Na_2SO_4$). The solvent is removed in vacuo to give a yellow oil (25.3 g). A 200 mg portion is further purified on Quantagram PQ1F plates (5% ethyl acetate/$CHCl_3$) to give 2,2-ethylenedioxy-6-hydroxy-6-methyl-5-oxo-1-tosyloxy-nonane (86 mg). ir (neat) 2.85μ (OH), 5.85μ (C=O), 6.25μ (C=C);

nmr ($CDCl_3$, δ), 0.88 (t, $CH_3CH_2$), 1.28 (s, $CH_3C\diagdown^{\diagup}$), 2.42

(s, 3H, $CH_3\phi SO_2$), 3.88 (s, 6H, $OCH_2CH_2O$ and $TsOCH_2C$), 7.47 (q, 4H, $CH_3\phi SO_2$).

When in the above procedure 2,2-ethylenedioxy-6-hydroxy-6-methyl-5,5-(1,3-propylenedithio)-1-tosyloxydecane and 2,2-ethylenedioxy-6-hydroxy-6-methyl-5,5-(1,3-propylenedithio)-1-tosyloxy-undecane are employed in place of 2,2-ethylenedioxy-6-hydroxy-6-methyl-5,5-(1,3-propylenedithio)-1-tosyloxy-nonane, the corresponding 2,2-ethylenedioxy-6-hydroxy-6-methyl-5-oxo-1-tosyloxy-decane and 2,2-ethylenedioxy-6-hydroxy-6-methyl-5-oxo-1-tosyloxy-undecane are obtained.

EXAMPLE 5

2,2-5,5-bis(Ethylenedioxy)-6-hydroxy-6-methyl-1-tosyloxynonane (6)

2,2-Ethylenedioxy-6-hydroxy-6-methyl-5-oxo-1-tosyloxynonane (24.8 g) is treated in benzene (1 l) with distilled ethylene glycol (45.5 ml) and p-toluenesulfonic acid (2.36 g) and the mixture is allowed to reflux (28 hours) in a Dean-Stark apparatus. The reaction mixture is cooled, sodium carbonate (4.3 g) is added and the resulting suspension is stirred for 0.5 hours and partitioned between ether (500 ml) and brine (500 ml). The aqueous phase is extracted with ether (300 ml) and the combined extracts are washed with brine (400 ml), filtered through phase-separating paper and dried ($Na_2SO_4$). The solvent is removed in vacuo to give a brown oil (23.55 g) which is purified via silica gel chromatography (ethyl acetate/$CHCl_3$) to give the crude product (13.3 g, 48%). A 200 mg portion is further purified via two preparative thin layer chromatography purifications (20% ethyl acetate/$CHCl_3$) to give 2,2-5,5-bis(ethylenedioxy)-6-hydroxy-6-methyl-1-tosyloxy-nonane (64 mg).

ir (neat) 2.8μ (OH);

nmr ($CDCl_3$, δ), 1.07 (s, $CH_3C\diagdown^{\diagup}$), 2.4 (s, 3H, $CH_3\phi SO_2$), 3.85 and 3.95 (m, 10H, $OCH_2CH_2O$ and $CH_3\phi SO_3CH_2C\diagdown^{\diagup}$), 7.5 (q, 4H, $CH_3\phi SO_3$).

When in the above procedure 2,2-ethylenedioxy-6-hydroxy6-methyl-5-oxo-1-tosyloxy-octane and 2,2-ethylenedioxy-6-hydroxy-6-methyl-5-oxo-1-tosyloxy-dodecane are employed in place of 2,2-ethylenedioxy-6-hydroxy-6-methyl-5-oxo-1-tosyloxy-nonane, the corresponding 2,2-5,5-bis (ethylenedioxy)-6-hydroxy-6-methyl-1-tosyloxy-octane and 2,2-5,5-bis (ethylenedioxy)-6-hydroxy-6-methyl-1-tosyloxy-dodecane are obtained.

EXAMPLE 6

3,3-6,6 bis(Ethylenedioxy)-2-methyl-2-n-propyl-oxepane (7)

2,2-5,5-bis(Ethylenedioxy)-6-hydroxy-6-methyl-1-tosyloxynonane (5.8 g) in distilled dimethylsulfoxide (90 ml) is treated with 99% sodium hydride (2.06 g) and the resulting mixture is allowed to stir 18 hours at 70° C. The reaction mixture is then poured into ice water (500 ml) and partitioned between hexane and brine. The aqueous phase is extracted with hexane and the combined extracts are washed with brine, filtered through phase-separating paper and dried ($Na_2SO_4$). The solvent is removed in vacuo to give a crude product (3.44 g). A 200 mg portion is purified via two preparative thin layer chromatography purifications using a total of 6 Quantagram PQ1F plates (20% ethyl acetate/$CHCl_3$) to give 3,3-6,6-bis(ethylenedioxy)-2-methyl-2-n-propyl-oxepane (35 mg).

nmr ($CDCl_3$, δ), 1.17 (s, $CH_3C\diagdown^{\diagup}$), 3.5 (d of d, 2H, $OCH_2C\diagdown^{\diagup}$), 3.88 and 3.98 (2s, 8H, 2x-$OCH_2CH_2O$).

When in the above procedure 2,2-5,5-bis(ethylenedioxy)-6-hydroxy-6-methyl-1-tosyloxy-tridecane and 2,2-5,5-bis(ethylenedioxy)-6-hydroxy-6-methyl-1-tosylox-ypentadecane are employed in place of 2,2-5,5-bis (ethylenedioxy)-6-hydroxy-6-methyl-1-tosyloxy-nonane the corresponding 3,3-6,6-bis(ethylenedioxy)-2-methyl-2-n-heptyl-oxepane and 3,3-6,6-bis(ethylenedioxy)-2-methyl-2-n-nonyl-oxepane are obtained.

EXAMPLE 7

6,6-Ethylenedioxy-2-methyl-2-n-propyl-oxepan-3-one (8)

3,3-6,6-bis(Ethylenedioxy)-2-methyl-2-n-propyl-oxepane (2.9 g) in ether (136 ml) is treated with 70% perchloric acid (3.3 ml) and allowed to stir at 35° C. for 3.5 hours. The reaction mixture is partitioned between ether and water, the aqueous phase is extracted with ether, and the combined ether layers are washed with brine and dried ($Na_2SO_4$). The solvent is removed in vacuo to give a dark brown oil (2.14 g). A duplicate run gives another 2.9 g of crude product. The crude products are combined and purified via silica gel chromatography (CHCl$_3$) to give crude product (2.8 g, 57%). A 200 mg portion is further purified on Quantagram PQ1F plates (20% ethyl acetate/CHCl$_3$) to give 6,6-ethylenedioxy-2-methyl-2-n-propyloxepan-3-one (64 mg).

ir (neat) 5.84μ (C=O);

nmr (CDCl$_3$, δ), 1.27 (s, CH$_3$C—), 3.45 (s, 2H, OCH$_2$C$\diagdown^\diagup$—), 3.98 (s, 4H, OCH$_2$CH$_2$O).

When in the above procedure 3,3-6,6-bis(ethylenedioxy)-2-methyl-2-n-butyl-oxepane and 3,3-6,6-bis(ethylenedioxy)-2-methyl-2-n-pentyl-oxepane are employed in place of 3,3-6,6-bis(ethylenedioxy)-2-methyl-2-n-propyl-oxepane, the corresponding 6,6-ethylenedioxy-2-methyl-2-n-butyl-oxepan-3-one and 6,6-ethylenedioxy-2-methyl-2-n-pentyl-oxepan-3-one are obtained.

EXAMPLE 8

2RS,3SR-6,6-Ethylenedioxy-3-hydroxy-2-methyl-2-n-propyl-oxepane and
2RS,3RS-6,6-ethylenedioxy-3-hydroxy-2-methyl-2-n-propyl-oxepane (9a and 9b)

6,6-Ethylenedioxy-2-methyl-2-n-propyl-oxepan-3-one (1.76 g) in methanol (250 ml) is treated with sodium borohydride (4.56 g) and the mixture is allowed to stir at 0° C. for 4 hours. The solvent is removed in vacuo and the resulting residue is dissolved in water and acidified with 10% hydrochloric acid to pH 3. The aqueous solution is extracted with ether, and the combined ether layers are washed with brine and dried (Na$_2$SO$_4$). The solvent is removed in vacuo to give an oil (1.57 g) which is purified via silica gel chromatography (hexane/chloroform) to give 2RS,3SR-6,6-ethylenedioxy-3-hydroxy-2-methyl-2-n-propyl-oxepane (682 mg); ir (KBr) 2.93μ (OH);

nmr (CDCl$_3$ δ), 1.16 (s, CH$_3$C$\diagdown^\diagup$—), 3.4–3.9 (m, OCH$_2$C$\diagdown^\diagup$— and CH$^\diagup$$^{OH}$    ), 3.88 (s, 4H, OCH$_2$CH$_2$O), mp 67–68°; and 2RS 3RS-6,6-ethylenedioxy-3-hydroxy-2-methyl-2-n-propyl-oxepane (395 mg); ir (KBr) 2.97 μ (OH); nmr (CDCl$_3$ δ), 1.16 (s, CH$_3$C$\diagdown^\diagup$—), 3.4–3.9 (m, OCH$_2$C$\diagdown^\diagup$— and —CH$^\diagup$$^{OH}$ . ), 3.88 (s, 4H, OCH$_2$CH$_2$O), mp 78–79°, and a mixture of the above alcohols (472 mg). When in the above procedure 6,6-ethylenedioxy-2-methyl-2-ethyl-oxepan-3-one and 6,6-ethylenedioxy-2-methyl-2-n-hexyl-oxepan-3-one are employed in place of 6,6-ethylenedioxy-2-methyl-2-n-propyl-oxepan-3-one the corresponding 2RS,3RS and 2RS,3SR-6,6-ethylenedioxy-3-hydroxy-2-methyl-2-ethyl-oxepane epimers and the 2RS,3RS and 2RS,3SR-6,6-ethylenedioxy-3-hydroxy-2-methyl-2-n-hexyl-oxepane epimers are obtained.

EXAMPLE 9

2RS,3SR-3-Acetoxy-2-methyl-2-n-propyl-oxepan-6-one (11a)

Acetyl chloride (0.49 ml) is added to a stirred solution of 2RS,3SR-6,6-ethylenedioxy-3-hydroxy-2-methyl-2-n-propyl-oxepane (217 mg) in benzene (25 ml) and pyridine (4.0 ml). The resulting suspension is stirred for 3 hours, poured into ice water and extracted with ether. The organic extract is washed with saturated copper sulfate solution and then with brine, filtered through phase-separating paper an dried (Na$_2$SO$_4$). The solvent is removed in vacuo to give a yellow liquid (246 mg) which is suitable for conversion to the ketone. The compound is further purified via preparative thin layer chromatography on Quantum PQ1F plates (25% ethyl acetate:hexane) to give 2RS,3SR-3-acetoxy-6,6-ethylenedioxy-2-methyl-2-n-propyl-oxepane.

nmr (CDCl$_3$ δ), 1.13 (s, 3H, CH$_3$—$\overset{|}{\underset{|}{C}}$—O), 2.03 (s, 3H, CH$_3$COO), 3.46 (s, 2H, —O—CH$_2$—C$\diagdown^{\diagup O}_{\diagdown O}$ ), 3.93 (s, 4H, —O—CH$_2$—CH$_2$—O—), 4.81 (m, 1H, C$_{3\beta}$—H).

A solution of 2RS,3SR-3-acetoxy-6,6-ethylenedioxy-2-methyl-2-n-propyl-oxepane (246 mg), anhydrous acetone (12.5 ml) and concentrated hydrochloric acid (0.25 ml) is heated at 45° C. for 3 hours. The acetone is removed in vacuo and the residue is partitioned between ether and brine. The aqueous layer is re-extracted with ether (3X) and the combined organic extract is washed well with brine (3X), filtered through phase-separating paper and dried (Na$_2$SO$_4$). The solvent is removed in vacuo to give 2RS,3SR-3-acetoxy-2-methyl-2n-propyl-oxepan-6-one as a yellow liquid (170 mg) which is suitable for use in the subsequent Wittig reaction.

When in the above procedure 2RS,3SR-6,6-ethylenedioxy-3-hydroxy-2-methyl-2-n-butyl-oxepane and 2RS,3SR-6,6-ethylenedioxy-3-hydroxy-2-methyl-2-n-hexyl-oxepane are employed in place of 2RS,3SR-6,6-ethylenedioxy-3-hydroxy-2-methyl-2-n-propyl-oxepane, the corresponding 2RS,3SR-3-acetoxy-2-n-butyl-2-methyl-oxepan-6-one and 2RS-3SR-3-acetoxy-2-n-hexyl-2-methyl-oxepan-6-one are obtained.

Alternatively, 2RS,3SR-3-acetoxy-2-methyl-2-n-propyl-oxepan-6-one can be obtained by the following route:

Acetyl chloride (1.1 ml) is added to a stirred solution of an approximate 1:1 mixture of 2RS,3SR-6,6-ethylenedioxy-3-hydroxy-2-methyl-2-n-propyl-oxepane and 2RS,3RS-6,6-ethylenedioxy-3-hydroxy-2-methyl-2-n-propyl-oxepane (484 mg) in benzene (50 ml) and pyridine (8.8 ml). Following the reaction procedure and work-up conditions described for the synthesis of 2RS,3SR-3-acetoxy-6,6-ethylenedioxy-2-methyl-2-n-propyl oxepane there is obtained a mixture of the corresponding epimeric acetates (561 mg), which is treated with concentrated hydrochloric acid (0.5 ml) in anhydrous acetone (25 ml) at 45° C. for 3 hours. Following the work-up procedure described for the synthesis of 2RS,3SR-3-acetoxy-2-methyl-2-n-propyl-oxepan-6-one there is obtained a yellow liquid (422 mg) which by thin layer chromatography contains a mixture of the epimeric keto-acetates. This mixture is purified by chromatography on silica gel using increasingly polar mixtures of ethyl acetate:hexane as the eluent to give 2RS,3SR-3-acetoxy-2-methyl-2-n-propyl-oxepan-6-one as a yellow liquid (113 mg).

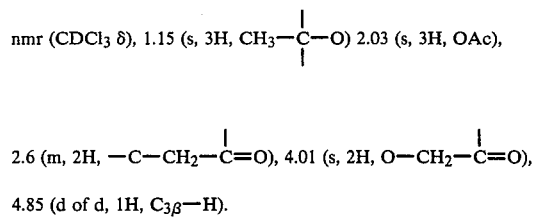

nmr (CDCl$_3$ δ), 1.15 (s, 3H, CH$_3$—C—O) 2.03 (s, 3H, OAc), 2.6 (m, 2H, —C—CH$_2$—C=O), 4.01 (s, 2H, O—CH$_2$—C=O), 4.85 (d of d, 1H, C$_{3\beta}$—H).

Further elution of the above column gives a mixture of the epimeric keto acetates (139 mg) and 2RS,3RS-3-acetoxy-2-methyl-2-n-propyl-oxepan-6-one (53 mg).

EXAMPLE 10

2RS,3RS-3-Acetoxy-2-methyl-2-n-propyl-oxepan-6-one (11b)

Acetyl chloride (1.13 ml) is added to a stirred solution of 2RS,3RS-6,6-ethylenedioxy-3-hydroxy-2-methyl-2-n-propyl-oxepane (501 mg) in benzene (50 ml) and pyridine (9.1 ml). The resulting suspension is stirred for 3 hours and an additional 0.2 ml of acetyl chloride is added. The suspension is stirred for an additional 2 hours, poured into ice water and extracted with ether. The organic extract is washed with saturated cupric sulfate solution and brine, filtered through phase-separating paper and dried (Na$_2$SO$_4$). The solvent is removed in vacuo to give a yellow liquid (567 mg) which is suitable for conversion to the ketone. The oil is further purified via preparative thin layer chromatography on Quantum PQ1F plates (30% ethyl acetate:hexane) to give 2RS,3RS-3-acetoxy-6,6-ethylenedioxy-2-methyl-2-n-propyl oxepane.

nmr (CDCl$_3$ δ), 1.18 (s, 3H, CH$_3$—C—O), 2.09 (s, 3H,

OAc), 3.5 (d of d, 2H, O—CH$_2$—C), 3.92 (broad s, 4H, O—CH$_2$—CH$_2$—O), 4.89 (broad m, 1H, C—3 H).

A solution of 2RS,3RS-3-acetoxy-6,6-ethylenedioxy-2-methyl-2-n-propyl oxepane (567 mg), anhydrous acetone (25 ml) and concentrated hydrochloric acid (0.5 ml) is heated at 45° C. for 3 hours. The acetone is removed in vacuo and the residue is partitioned between ether and brine. The aqueous layer is reextracted with ether (3X) and the combined organic extract is washed well with brine (3X), filtered through phase-separating paper and dried (Na$_2$SO$_4$). The solvent is removed in vacuo to give a yellow liquid (391 mg) which is suitable for use in the subsequent Wittig reaction. The compound is further purified via preparative thin layer chromatography on Quantum PQ1F plates (30% ethyl acetate:hexane) to give 2RS,3RS-3-acetoxy-2-methyl-2-n-propyl-oxepan-6-one.

nmr (CDCl$_3$ δ), 1.20 (s, 3H, CH$_3$—C—O), 2.07 (s, 3H,

OAc), 2.63 (m, 2H, —CH$_2$—C=O), 4.03 (s, 2H, O—CH$_2$—C=O), 4.83 (t, 1H, C—3α—H);

ir (neat), 5.75, 5.83μ (C=O).

When in the above procedure 2RS,3RS-6,6-ethylenedioxy-3-hydroxy-2-methyl-2-n-pentyl-oxepane and 2RS,3RS-6,6-ethylenedioxy-3-hydroxy-2-methyl-2-n-heptyl-oxepane are employed in place of 2RS,3RS-6,6-ethylenedioxy-3-hydroxy-2-methyl-2-n-propyl-oxepane the corresponding 2RS,3RS-3-acetoxy-2-methyl-2-n-pentyl-oxepan-6-one and 2RS,3RS-3-acetoxy-2-methyl-2-n-heptyl-oxepan-6-one are obtained.

EXAMPLE 11

2RS,3SR-3-Acetoxy-6-carboethoxymethylidene-2-methyl-2-n-propyl oxepane (13a)

Triethyl phosphonoacetate (728 mg) is added dropwise to a suspension of sodium hydride (99%, 68 mg) in anhydrous benzene (25 ml). The suspension is heated to 70° and stirred vigorously until the evolution of hydrogen ceases. A solution of 2RS,3SR-3-acetoxy-2-methyl-2-n-propyl-oxepan-6-one (260 mg) in anhydrous benzene (3 ml) is added slowly to the above solution and heated at 70°–75° C. for 1 hour. The resulting solution is cooled, ether (150 ml) and 10% hydrochloric acid (35 ml) are added and the organic layer is separated. The aqueous layer is re-extracted with ether (3X) and the combined organic extract is washed with brine (3X), filtered through phase-separating paper and dried (sodium sulfate). The solvent is removed in vacuo to give a residue (1.01 g) which contains 2RS,3SR-3-acetoxy-6-carboethoxymethylidene-2-methyl-2-n-propyl oxepane as the major component and a large quantity of excess triethyl phosphonoacetate. The residue is purified via silica gel chromatography (1% ethyl acetate:hexane) to give the pure product (265 mg, 78%).

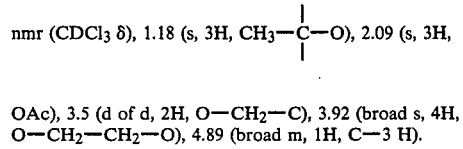

nmr (CDCl$_3$ δ), 1.17 (s, CH$_3$—C—O, 3), 1.26 (t, CH$_3$CH$_2$, 3H), 2.04 (s, OAc, 3H), 3.9–4.3 (overlapping q and s, CH$_3$CH$_2$ and trans- O—CH$_2$—C=), 4.8 (overlapping m, C—3-β-H and cis- O—CH$_2$—C=), 5.65 (broad s, =CH—CO$_2$Et, 1H).

When in the above procedure 2RS,3SR-3-acetoxy-2-methyl-2-n-butyl-oxepan-6-one and 2RS,3SR-3-acetoxy-2-methyl-2-n-pentyl-oxepan-6-one are employed in place of 2RS,3SR-3-acetoxy-2-methyl-2-n-propyl-oxepan-6-one the corresponding 2RS,3SR-3-acetoxy-6-carboethoxymethylidene-2-methyl-2-n-butyl oxepane and 2RS,3SR-3-acetoxy-6-carboethoxymethylidene-2-methyl-2-n-pentyl oxepane are obtained.

EXAMPLE 12

2RS,3RS-3-Acetoxy-6-carboethoxymethylidene-2-methyl-2-n-propyl-oxepane (13b)

Triethyl phosphonoacetate (1.23 g) is added dropwise to a suspension of sodium hydride (99%, 116 mg) in anhydrous benzene (40 ml). The suspension is heated to 70° and stirred until the evolution of hydrogen ceases. A solution of 2RS,3RS-3-acetoxy-2-methyl-2-n-propyl-oxepan-6-one (440 mg) in anhydrous benzene (4 ml) is added slowly to the above solution and heated at 70°–75° for 1 hour. The resulting solution is cooled, ether (200 ml) and 10% HCl (50 ml) are added and the organic layer is separated. The aqueous layer is re-extracted with ether (3X) and the combined organic extract is washed with brine (3X), filtered through phase-separating paper and dried (sodium sulfate). The solvent is removed in vacuo to give a residue (1.4 g) which is chromatographed on 25 g of silica gel (1% ethyl acetate:hexane) to give 2RS,3RS-3-acetoxy-6-carboethoxymethylidene-2-methyl-2-n-propyl-oxepane (443 mg, 77%); m.p.=65°–66°, (from hexane);

nmr (CDCl₃ δ), 1.13 (s, CH₃—C—O, 3), 1.25

(t, CH₃CH₂, 3H), 2.07 (s, OAc, 3H), 3.9–4.3 (overlapping q and broad s, CH₃CH₂ and trans-O—CH₂—C=), 4.8

(overlapping m, C—3-α-H and cis-O—CH₂—C=), 5.63

(broad s, =CH—CO₂Et, 1H).

When in the above procedure 2RS,3RS-3-acetoxy-2-methyl-2-n-butyl-oxepan-6-one and 2RS,3RS-3-acetoxy-2-methyl-2-n-pentyl-oxepan-6-one are employed in place of 2RS,3RS-3-acetoxy-2-methyl-2-n-propyl-oxepan-6-one, the corresponding 2RS,3RS-3-acetoxy-6-carboethoxymethylidene-2-methyl-2-n-butyloxepane and 2RS,3RS-3-acetoxy-6-carboethoxymethylidene-2-methyl- 2-n-pentyl-oxepane are obtained.

EXAMPLE 13

1RS,4SR,5RS-4-Methyl-4-n-propyl-3,8-dioxabicyclo[3.2.1] octane-1-acetic acid, ethyl ester (12a)

A solution of sodium ethoxide in ethanol (prepared from 8.7 mg of sodium in 1 ml of absolute alcohol) is cooled to 0° C. and triethyl phosphonoacetate (87 mg) in absolute alcohol (1 ml) is added and stirred for 15 minutes. A mixture of 2RS,3SR-3-acetoxy-2-methyl-2-n-propyl-oxepan-6-one and 2RS,3RS-3-acetoxy-2-methyl-2-n-propyl-oxepan-6-one (86 mg) in ethanol (1 ml) is added dropwise and then stirred at 20° C. for 0.5 hours. The solution is diluted with brine and extracted with ether. The ether extract is dried (Na₂SO₄) and evaporated in vacuo to give a residue (81 mg) which is chromatographed via preparative thin layer chromatography on Quantum PQ1F plates (30% ethyl acetate:hexane) to give a mixture having the following nmr spectrum:

nmr for the mixture: (CDCl₃ δ), 1.13 and 1.17 (2s,

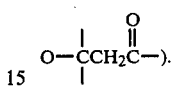
3H, CH₃C—O), 2.04 and 2.07 (2s, 3H, —OCOCH₃), 3.3–3.9 (d of d, 2H, OCH₂C—O), 2.6 (s, 2H,

O—CCH₂C—).

The mass spec. for one of the compounds shows two epimers with identical mass spectra, M+256, i.e. 1RS,4SR,5RS-4-methyl-4-n-propyl-3,8-dioxabicyclo[3.2.1]octane-1-acetic acid, ethyl ester and 1RS,4RS,5RS-4-methyl-4-n-propyl-3,8-dioxabicyclo[3.2.1]octane-1-acetic acid, ethyl ester.

The mass spec. for the second compound also shows two epimers having a mass spectra identical to 2RS,3SR-3-acetoxy-6-carboethoxymethylidene-2-methyl-2-n-propyl-oxepane and 2RS,3RS-3-acetoxy-6-carboethoxymethylidene-2-methyl-2-n-propyl-oxepane. The epimers are obtained in pure form by chromatography.

When in the above procedure a mixture of 2RS,3SR-3-acetoxy-2-methyl-2-ethyl-oxepan-6-one and 2RS,3RS-3-acetoxy-2-methyl-2-ethyl-oxepan-6-one, 2RS,3SR-2RS,3RS-3-acetoxy-2-methyl-2-n-pentyloxepan-6-one and 2RS,3SR-2RS,3RS-3-acetoxy-2-methyl-2-n-heptyl-oxepan-6-one are employed in place of 2RS,3SR-2RS,3RS-3-acetoxy-2-methyl-2-n-propyl-oxepan-6-one, the corresponding 1RS,4SR,5RS-4-methyl-4-ethyl-3,8-dioxabicyclo[3.2.1]octane-1-acetic acid, ethyl ester; 1RS,4SR,5RS-4-methyl-4-n-pentyl-3,8-dioxabicyclo[3.2.1]octane-1-acetic acid, ethyl ester; and 1RS,4SR,5RS-4-methyl-4-n-heptyl-3,8-dioxabicyclo[3.2.1]octane-1-acetic acid, ethyl ester are obtained.

Where applicable, in all of the above examples

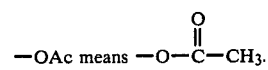
—OAc means —O—C—CH₃.

EXAMPLE 14

1RS,4SR,5RS-4-Methyl-4-n-pentyl-3,8-dioxabicyclo[3.2.1] octane-1-acetic acid (II)

Aqueous sodium hydroxide (0.2N, 5 ml) is added within two minutes to 1RS,4SR,5RS-4-methyl-4-n-pentyl-3,8-dioxabicyclo[3.2.1]octane-1-acetic acid ester (860 mg, 3.0 mole) in methanol (5 ml) while stirring at 0° C. under nitrogen. The solution is allowed to come to +20°, and stirring is continued for three days under nitrogen. The solvent is evaporated in vacuo and the residue is extracted with methylene chloride. The extract is back-extracted with water, then with sodium chloridewater. The basic, aqueous solution is carefully acidified with 2N aqueous hydrochloric acid (5.0 ml). The cloudy solution is extracted with methylene chloride and the extract is washed with water and with aqueous sodium chloride, dried (Na₂SO₄) and filtered through celite on a sintered glass funnel to give 1RS,4SR,5RS-4-methyl-4-n-pentyl-3,8-dioxabicyclo[3.2.1]octane-1-acetic acid (762.7 mg).

IR (CDCl$_3$) 3100–3600, 2400–2600 (OH), 1750 and 1715 (CO of acid), NMR (CDCl$_3$)δ:

3.88 (t, 1H, —O—CH—CH$_2$—), 3.60 (q, 2H, —O—CH$_2$—C—O—), 2.63 (br.s., 2H, —CH$_2$—CO$_2$H), 1.92–2.08 (m, 4H,

—CH$_2$—CH$_2$—), 1.33 (s, 3H, CH$_3$—C—O—), 0.88 (dist'd t, 3H,

CH$_3$(CH$_2$)$_5$—).

Preparation of starting material:

PREPARATION A

5-Benzyloxy-4-hydroxypentanal diethyl acetal

A solution of 5-benzyloxy-4-hydroxy-2-pentynal diethyl acetal (43.2 g) in abs. ethanol (250 ml) is hydrogenated in the presence of 82.7% platinum oxide (1.4 g), sodium nitrite (14 mg) and 1 drop of water for 90 minutes in a Parr hydrogenation apparatus. The reaction is repeated exactly as above with another portion (43.2 g) of 5-benzyloxy-4-hydroxy-2-pentynal diethyl acetal; the two mixtures are combined and the catalyst is removed by filtration through a bed of celite and washed with ethanol. The combined filtrate is evaporated in vacuo to give a residue (89.4 g, 100%). A 200 mg portion of the residue is purified on Quantagram PQ1F plates (developed in 40% CHCl$_3$/hexane three successive times). The principal band is eluted with ethyl acetate and the solvent is evaporated in vacuo to give 5-benzyloxy-4-hydroxypentanal diethyl acetal (152 mg); ir (neat) 2.88μ (OH);

nmr (CDCl$_3$, δ): 1.17 (t, 6H, OCH$_2$CH$_3$), 1.62 (m, 4H, CHCH$_2$CH$_2$CH), 2.7 (b, 1H, >CH—OH), 3.53 (m, 7H, OCH$_2$CH$_3$ and OCH$_2$CH and —CH(O)(O)), 4.47 (m, 1H, >CHOH), 4.5 (s, 2H φCH$_2$O), 7.28 (s, 5H, φCH$_2$O).

PREPARATION B

5-Benzyloxy-1,1-diethoxy-pentan-4-one

Chromium trioxide (193 g) is added to a slurry of methylene chloride (6.9 l), dry pyridine (308 ml) and dry celite (402 g). After stirring for 45 minutes, 5-benzyloxy-4-hydroxypentanal diethyl acetal (88.9 g) in methylene chloride (950 ml) is added dropwise and the mixture is stirred overnight at room temperature. The celite and the salts are removed by filtration and washed with methylene chloride (9 l). The solvent is removed in vacuo and the filter cake is washed further with diethyl ether (9 l). The ether layer is added to the methylene chloride residue; the mixture is stirred for one hour, and filtered through a bed of celite. The filtrate is washed with 5% sodium bicarbonate (4 l), brine (3 l) and dried (sodium sulfate). After removal of most of the ether, the pyridine is removed with saturated copper sulfate (600 ml), and the ether layer is washed with brine (300 ml) and dried (sodium sulfate). The solvent is removed in vacuo to give an oil (85.2 g, 96.5%). A 200 mg portion of the residue is purified on Quantagram PQ1F plates (20% ethyl acetate/chloroform) to give 5-benzyloxy-1,1-diethoxy-pentan-4-one (200 mg); ir (neat) 5.79μ (C=O):

nmr (CDCl$_3$, δ): 1.17 (t, 6H, OCH$_2$CH$_3$), 1.9 (m, 2H, CH$_2$CH$_2$CH), 2.52 (t, 2H, CH$_2$CH$_2$CH), 3.48 (m, 4H, OCH$_2$CH$_3$), 4.03 (s, 2H, OCH$_2$CO), 4.45 (t, 1H, —CH(O)(O)), 4.53 (s, 2H, φCH$_2$O), 7.28 (s, 5H, φCH$_2$O).

PREPARATION C

1-Benzyloxy-4-(1,3-dithian-2-yl)-butan-2-one

5-Benzyloxy-1,1-diethoxy-pentan-4-one (84.7 g) is treated in chloroform (150 ml) with 1,3-propanedithiol (33.2 g) and immediately cooled in an ice water bath. After the addition of zinc chloride (41 g) the mixture is stirred overnight at room temperature, poured into brine (1.2 l) and allowed to stir for an additional hour. The organic layer is separated, washed with 5% potassium hydroxide (1 l), brine (1.5 l) and dried (sodium sulfate). The solvent is removed in vacuo to give a yellow oil (90 g, 100%). A 250 mg portion of the oil is purified on Quantagram PQ1F plates (chloroform) to give 1-benzyloxy-4-(1,3-dithian-2-yl)-butan-2-one (230 mg); ir (neat) 5.78μ (C=O);

nmr (CDCl$_3$, δ): 1.97 (m, 4H, SCH$_2$CH$_2$CH$_2$S and CH$_2$CH$_2$CH), 2.73 (m, 6H, SCH$_2$CH$_2$CH$_2$S and —CCH$_2$CH$_2$), 3.95 (t, 1H, —CH(S)(S)), 4.03 (s, 2H, OCH$_2$C), 4.53 (s, 2H, φCH$_2$O), 7.28 (s, 5H, aromatic H).

PREPARATION D

1-Benzyloxy-2,2-ethylenedioxy-4-(1,3-dithian-2-yl)-butane

Treatment of 1-benzyloxy-4-(1,3-dithian-2-yl)-butan-2-one (89.8 g) in benzene (3.5 l) with distilled ethylene glycol (220 ml) and p-toluenesulfonic acid (11.7 g) at reflux temperature in a Dean-Stark apparatus for 18 hours gives a mixture which is concentrated to 500 ml in vacuo and allowed to stir for one hour. After the addition of sodium carbonate (10 g), the mixture is then partitioned between ether (300 ml) and brine (300 ml). The aqueous phase is extracted with ether (600 ml) and the combined extracts are washed with 0.05% sodium carbonate (1.2 l), filtered through phase-separating paper and dried (sodium sulfate). The solvent is removed in vacuo to give a residue (102.15 g; 99%). A 200 mg portion of the residue is purified on Quantagram PQ1F plates (chloroform) to give 1-benzyloxy-2,2-ethylenedioxy-4-(1,3-dithian-2-yl)-butane (180 mg);

nmr (CDCl₃, δ) 1.92 (m, 6H, CCH₂CH₂CH and

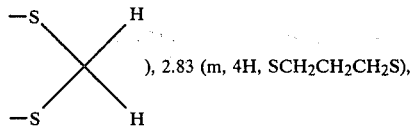

), 2.83 (m, 4H, SCH₂CH₂CH₂S),

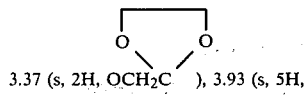

3.37 (s, 2H, OCH₂C ), 3.93 (s, 5H,

OCH₂CH₂O and —CH ), 4.55 (s, 2H, φCH₂O), 7.28 (s, 5H, φCH₂O).

We claim:
1. A compound of the formula

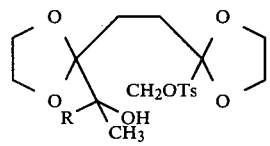

wherein R is a straight or branched chain alkyl group having 2–10 carbon atoms and Ts is a tosyl group.
2. The compound of claim 1 wherein R is pentyl.
3. The compound of claim 1 wherein R is propyl.

* * * * *